United States Patent [19]

Sutton et al.

[11] 3,947,565

[45] Mar. 30, 1976

[54] ANTI-ARTHRITIC COMPOSITIONS COMPRISING S-HETEROCYCLIC DERIVATIVES OF PHOSPHINE OR PHOSPHITE GOLD MERCAPTIDES AND METHODS OF PRODUCING ANTI-ARTHRITIC ACTIVITY

[75] Inventors: Blaine M. Sutton, Hatboro; Joseph Weinstock, Phoenixville, both of Pa.

[73] Assignee: SmithKline Corporation, Philadelphia, Pa.

[22] Filed: Jan. 22, 1975

[21] Appl. No.: 542,976

Related U.S. Application Data

[62] Division of Ser. No. 384,666, Aug. 1, 1973, Pat. No. 3,883,546.

[52] U.S. Cl. .................................................. 424/200
[51] Int. Cl.² .................................... A61K 31/675
[58] Field of Search ........................... 424/200

[56] References Cited
UNITED STATES PATENTS

| | | | |
|---|---|---|---|
| 3,502,690 | 3/1970 | Schroder et al. | 260/299 |
| 3,755,329 | 8/1973 | Vaughan | 260/299 |

*Primary Examiner*—Stanley J. Friedman
*Attorney, Agent, or Firm*—Janice E. Williams; Richard D. Foggio; William H. Edgerton

[57] ABSTRACT

S-Heterocyclic derivatives of phosphine or phosphite gold mercaptides having anti-arthritic activity are disclosed.

14 Claims, No Drawings

ANTI-ARTHRITIC COMPOSITIONS COMPRISING S-HETEROCYCLIC DERIVATIVES OF PHOSPHINE OR PHOSPHITE GOLD MERCAPTIDES AND METHODS OF PRODUCING ANTI-ARTHRITIC ACTIVITY

This is a division of application Ser. No. 384,666 filed Aug. 1, 1973, now U.S. Pat. No. 3,883,546.

This invention relates to novel S-heterocyclic derivatives of phosphine or phosphite gold mercaptides which have useful pharmacological activity. More specifically, the compounds of this invention have anti-arthritic activity as measured by their ability to inhibit adjuvant-induced polyarthritis in rats.

The compounds of this invention are represented by the following structural formula:

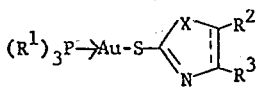

FORMULA I in which
$R^1$ is lower alkyl, lower alkoxy, phenyl or phenoxy, with each alkyl or alkoxy having from one to three carbon atoms;

X is S, NH, $NCH_3$ or O;

$R^2$ and $R^3$ are hydrogen or together form a 1,2-benzo radical; and

=indicates an optional double bond.

Preferred compounds of this invention are represented by Formula I where R is lower alkyl. Also preferred are those compounds of Formula I where the heterocyclic moiety is 2-thiazolinyl, 2-benzimidazolyl and 2-benzoxazolyl.

The compounds of this invention are prepared by reaction of an heterocyclic mercaptan compound with an appropriate phosphine or phosphite gold(I) halide, preferably chloride, in the presence of alkali such as sodium hydroxide in a solvent such as aqueous alcohol-chloroform at about 25° for approximately one hour in a nitrogen atmosphere.

The phosphine or phosphite gold halides employed as starting materials are prepared by reaction of a cold (−10° to −5°) solution of gold(I) chloride, prepared by mixing thiodiglycol and gold acid chloride trihydrate in aqueous alcohol, with an appropriate phosphine or phosphite such as triethylphosphine. Other procedures which may be applied to the preparation of these intermediates are found in J. Chem. Soc. 1828 (1937) and 1235 (1940) and Australian J. Chem. 19:547 (1966).

The anti-arthritic activity of the compounds of this invention is measured by their ability to inhibit adjuvant-induced polyarthritis in rats. The compounds of Formula I produce marked inhibition of the developement of adjuvant arthritis in rats at daily oral doses as low as about 20 mg. per kilogram of body weight. Of particular importance is the attainment of significant serum levels of gold following oral administration of these doses.

Adjuvant arthritis in rats is produced by a single injection of 0.75 mg. of Mycobacterium butyricum suspended in white paraffin (N.F.) into a hindpaw (left footpad). The injected leg becomes inflamed and reaches a maximum volume in three to five days (primary lesion). The animals exhibit a decrease in body weight gain during this initial period. Adjuvant arthritis (secondary phase) occurs after a delay of approximately 10 days and is characterized by inflammation of the non-injected sites (right hind leg), decrease in body weight gain and further increases in the volume of the injected hind leg. The compounds of Formula I administered in the doses described above beginning on the day of adjuvant injection and continuing for 17 days thereafter, exclusive of days 4, 5, 11 and 12, protect the animals against development of both primary and secondary lesions of adjuvant arthritis.

The compounds of this invention are administered in conventional dosage unit forms by incorporating an amount sufficient to produce anti-arthritic activity, without toxic effects, with a nontoxic pharmaceutical carrier according to accepted procedures. Preferably the dosage units will contain an S-heterocyclic derivative of a phosphine or phosphite gold mercaptide of Formula I in an amount of from about 0.5 mg. to about 25 mg., preferably 0.5 mg. to 10 mg. calculated on gold content, per unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or an aqueous or nonaqueous liquid suspension.

The method of producing anti-arthritic activity in accordance with this invention comprises administering internally to an animal organism an S-heterocyclic derivative of a phosphine or phosphite gold mercaptide of Formula I, usually combined with a pharmaceutical carrier, in an amount sufficient to produce anti-arthritic activity without limiting side effects. The active medicament will be administered in a dosage unit, as described above, orally or parenterally, the oral route being preferred. Advantageously equal doses will be administered one or two times daily with the daily dosage regimen being from about 0.5 mg. to about 50 mg., preferably 0.5 mg. to about 20 mg., calculated on gold content. When the method described above is carried out, anti-arthritic activity is produced with a minimum of side effects.

The pharmaceutical preparations are made following the conventional techniques of the pharmaceutical chemist involving mixing, granulating and compressing when necessary, or variously mixing and dissolving the ingredients as appropriate to the desired end product.

The following examples illustrate the preparation of compounds of this invention and their incorporation into pharmaceutical compositions, and as such are not to be construed as limiting the invention set forth in the claims appended hereto. Temperatures are in degrees Centigrade unless otherwise stated.

EXAMPLE 1

2-Thiazolinylthio(triethylphosphine)gold

A solution of 10.0 g. (0.08 mol.) of thiodiglycol in 25 ml. of ethanol was mixed with a solution of 15.76 g. (0.04 mol.) of gold acid chloride trihydrate in 75 ml. of distilled water. When the bright orange-yellow solution was almost colorless, it was cooled to below −5° and an equally cold solution of 5.0 g. (0.0425 mol.) of triethylphosphine in 25 ml. of ethanol was added dropwise to the stirred solution. After the addition was complete, the cooled mixture was stirred for 30 minutes. The solid that separated was removed by filtration and the filtrate was concentrated to about 30 ml. to yield a second crystal crop. The combined solid was washed with 2:1 aqueous ethanol and recrystallized from ethanol by addition of water to the cloud point to give chloro(triethylphosphine)gold, m.p. 85°–86°.

To a solution of 0.8 g. (0.02 mol.) of sodium hydroxide in 20 ml. of 1:1 aqueous ethanol was added a solution of 2.4 g. (0.02 mol.) of 2-mercaptothiazoline in 20 ml. of 1:1 ethanol-chloroform followed by a solution of 7.0 g. (0.02 mol.) of chloro(triethylphosphine)gold in 40 ml. of 1:1 ethanol-chloroform. The reaction mixture was stirred under nitrogen at 25° for 1 hour, then it was filtered and the filtrate was evaporated to dryness. Chloroform was added to the residue and the solution was again evaporated to dryness to give a thick yellow liquid which crystallized when triturated with acetone and cooled over dry ice to give the title compound, m.p. 70°–71° (acetone-water).

EXAMPLE 2

2-Benzimidazolylthio(triethylphosphine)gold

To a solution of 0.4 g. (0.01 mol.) of sodium hydroxide in 20 ml. of 1:1 aqueous ethanol was added 1.5 g. (0.01 mol.) of 2-mercaptobenzimidazole in 20 ml. of ethanol followed by 3.5 g. (0.1 mol.) of chloro(triethylphosphine)gold in 20 ml. of 1:1 chloroform-ethanol. The reaction mixture was stirred for 1 hour at 25° under nitrogen, then it was filtered and the filtrate evaporated to dryness to give the title compound as a white solid, m.p. 222°–223° (ethanol).

EXAMPLE 3

2-Benzoaxolythio(triethylphosphine)gold

To a solution of 0.6 g. (0.015 mol.) of sodium hydroxide in 20 ml. of 1:1 aqueous ethanol was added 2.28 g. (0.015 mol.) of 2-mercaptobenzoxazole in 20 ml. of ethanol followed by 5.25 g. (0.015 mol.) of chloro(triethylphosphine)gold in 40 ml. of 1:1 ethanol-chloroform. The reaction mixture was stirred at 25° for 1 hour under nitrogen, filtered and the filtrate was evaporated to dryness to give a residue which was dissolved in methanol and treated with activated charcoal to give the title compound as white crystals, m.p. 100°–102° (methanol).

EXAMPLE 4

A solution of 2.44 g. (0.02 mol.) of thiodiglycol in 15 ml. of methanol was mixed with a solution of 3.98 g. (0.01 mol.) of gold acid chloride trihydrate in 25 ml. of distilled water. When the orange-yellow solution became almost colorless, it was cooled to −15° and an equally cold solution of 760 mg. (0.01 mol.) of trimethylphosphine in 10 ml. of methanol was added dropwise to the stirred solution. After the addition, the cooled mixture was stirred for 30 minutes, then the product was filtered off and the filtrate was concentrated in vacuo to give a second crystal crop. The combined solid material was washed with cold aqueous methanol (2:1) and water to give chloro(trimethylphosphine)gold, m.p. 228°–229°.

When an equivalent amount of (chloro(trimethylphosphine)gold is substituted in the procedure of Example 1 for chloro)triethylphosphine)gold, 2-thiazolinylthio)trimethylphosphine)gold is obtained.

In like manner, substitution of an equivalent amount of chloro(trimethylphosphine)gold in the procedures of Examples 2 and 3 for chloro(triethylphosphine)gold gives 2-benzimidazolylthio(trimethylphosphine)gold and 2-benzoxazolylthio (trimethylphosphine)gold, respectively.

EXAMPLE 5

A mixture of 11.82 g. (0.03 mol.) of gold acid chloride trihydrate and 1.9 g. (0.065 mol.) of thiodiglycol in 100 ml. of aqueous ethanol (3:2) was stirred until the color of auric gold disappeared. The almost colorless solution was cooled below −5° and an equally cold solution of 5.6 g. (0.035 mol.) of triisopropylphosphine in 20 ml. of ethanol was added dropwise. The volume of the final reaction mixture was increased to 250 ml. with 1:1 aqueous ethanol in order to maintain a fluid mixture. After addition the mixture was stirred in the cold for 45 minutes. The solid was removed by filtration, washed with 1:2 alcohol-water and water and dried (MgSO$_4$), then redissolved by suspension in ethanol and addition of sufficient methylene chloride to attain solution. The cloudy solution was filtered from suspended gold and the filtrate was concentrated to give chloro(triisopropylphosphine)gold as white crystals, m.p. 184°–186°.

Substitution of an equivalent amount of chloro(triisopropylphosphine)gold in the procedure of Example 1 for chloro(triethylphosphine)gold gives 2-thiazolinylthio(triisopropylphosphine) gold.

Similarly, when an equivalent amount of chloro(triisopropylphosphine) gold is substituted in the procedure of Example 2 for chloro(triethylphosphine)gold, 2-benzimidazolylthio (triisopropylphosphine)gold is obtained.

In like manner, 2-benzoxazolylthio(triisopropylphosphine) gold is prepared by substitution of an equivalent amount of chloro(triisopropylphosphine)gold in the procedure of Example 3 for chloro(triethylphosphine)gold.

EXAMPLE 6

Gold acid chloride trihydrate (4.0 g; 0.01 mol.) was reduced to aurous chloride with 2.44 g. of thiodiglycol in 1:2 aqueous ethanol. After cooling the solution in an ice bath, a cold solution of 2.26 g. (0.01 mol.) of triphenylphosphine in a minimum amount of ethanol was added with stirring. The reaction mixture was stirred for 30 minutes, then it was filtered and the solid product was washed with cold aqueous alcohol and ice water and dried to give chloro(triphenylphosphine) gold, m.p. 242°–243°.

When an equivalent amount of chloro(triphenylphosphine) gold is substituted in the procedure of Example 1 for chloro(triethylphosphine)gold, 2-thiazolinylthio(triphenylphosphine) gold is obtained.

Likewise, 2-benzimidazolylthio(triphenylphosphine)- gold and 2-benzoxazolylthio(triphenylphosphine)gold are obtained by substitution of equivalent amounts of chloro(triphenylphosphine) gold in the procedures of Examples 2 and 3, respectively, for chloro(triethylphosphine)gold.

EXAMPLE 7

Gold acid chloride trihydrate (3.58 g.; 0.009 mol.) was reduced to aurous chloride with 3.29 g. (0.027 mol.) of thiodiglycol in 70 ml. of water saturated with sodium chloride. To the fresh solution was added 1.52 g. (0.009 mol.) of diethylphenylphosphine in 20 ml. of ethanol and the reaction mixture was stirred for one hour at 25° under a nitrogen atmosphere. The reaction mixture was then extracted with chloroform and the extract was washed with water and dried ($MgSO_4$). Concentration gave a residue which was chromatographed on silica gel with benzene and chloroform to give chloro(diethylphenylphosphine)gold.

When an equivalent amount of chloro(diethylphenylphosphine)gold is substituted in the procedure of Example 1 for chloro(triethylphosphine)gold, 2-thiazolinylthio(diethylphenylphosphine)gold is obtained.

Likewise, 2-benzimidazolylthio(diethylphenylphosphine)gold and 2-benzoxazolylthio(diethylphenylphosphine)gold are obtained by substitution of equivalent amounts of chloro(diethylphenylphosphine)gold in the procedures of Examples 2 and 3, respectively, for chloro(triethylphosphine)gold.

EXAMPLE 8

By following procedures outlined in J. Chem. Soc. 1828 (1937), iodo(trialkylphosphine)gold complexes are prepared, for example, iodo(triethylphosphine)gold.

When an equivalent amount of iodo(triethylphosphine)gold is substituted in the procedure of Example 1 for chloro(triethylphosphine)gold, 2-thiazolinylthio(triethylphosphine)gold is obtained.

Similarly, by following procedures outlined in J. Chem. Soc. 1235 (1940), bromo(trialkylphosphine)gold complexes are prepared, for example, bromo(triethylphosphine)gold.

Substitution of an equivalent amount of bromo(triethylphosphine)gold in the procedure of Example 1 for chloro(triethylphosphine)gold also gives 2-thiazolinylthio(triethylphosphine)gold.

By similar procedures, the other S-heterocyclic derivatives of phosphine gold mercaptides of Formula I may be prepared as described from the appropriate phosphine gold(I) iodides and bromides.

EXAMPLE 9

Gold acid chloride trihydrate (5.9 g.; 0.015 mol.) is reduced to aurous chloride with 3.7 g. (0.03 mol.) of thiodiglycol in 1:2 aqueous ethanol. The solution is cooled to −10° and an equally cold solution of 3.72 g. (0.02 mol.) of triethylphosphite in 20 ml. of ethanol is added dropwise with stirring. The temperature is maintained at −10° and stirring is continued for 30 minutes. The ethanol is removed from the reaction mixture under reduced pressure without heating and the aqueous residue is then extracted with methylene chloride. The extract is dried and the solvent evaporated in vacuo. The crude product is purified by chromatography on a silica gel column to give chloro(triethylphosphite) gold as an oil.

Substitution of an equivalent amount of chloro(triethylphosphite) gold in the procedure of Example 1 for chloro(triethylphosphine)gold gives 2-thiazolinylthio(triethylphosphite) gold.

When an equivalent amount of chloro(triethylphosphite) gold is substituted in the procedure of Example 2 for chloro(triethylphosphine)gold, 2-benzimidazolylthio(triethylphosphite)gold is obtained.

Similarly, substitution of an equivalent amount of chloro(triethylphosphite)gold in the procedure of Example 3 for chloro(triethylphosphine)gold gives 2-benzoxazolylthio(triethylphosphite)gold.

EXAMPLE 10

Gold acid chloride trihydrate (4.0 g.; 0.01mol.) was reduced to aurous chloride with 2.44 g. of thiodiglycol in 1:2 aqueous methanol. The solution was cooled in an ice bath and a cold solution of 1.5 g. of trimethylphosphite in 10 ml. of methanol was added dropwise with stirring under nitrogen. The reaction mixture was stirred for 30 minutes, filtered and the solid was washed with cold aqueous methanol and dried. The product was dissolved in 5 ml. of chloroform and this solution was diluted with 10 ml. of methanol and filtered through charcoal. The filtrate was concentrated under reduced pressure and the residue was cooled and diluted with ice-water to precipitate chloro(trimethylphosphite)gold, m.p. 99°–100°.

When an equivalent amount of chloro(trimethylphosphite) gold is substituted in the procedures of Examples 1, 2 and 3 for chloro(triethylphosphine)gold, 2-thiazolinylthio(trimethylphosphite)gold, 2-benzimidazolylthio(trimethylphosphite)gold and 2-benzoxazolylthio(trimethylphosphite)gold are obtained, respectively.

EXAMPLE 11

When an equivalent amount of triphenylphosphite is substituted in the procedure of Example 10 for trimethylphosphite, chloro(triphenylphosphite)gold is obtained.

Substitution of an equivalent amount of chloro(triphenylphosphite)gold in the procedure of Example 1 for chloro(triethylphosphine)gold gives 2-thiazolinylthio(triphenylphosphite)gold.

In like manner, when an equivalent amount of chloro(triphenylphosphite)gold is substituted in the procedures of Examples 2 and 3 for chloro(triethylphosphine)gold 2-benzimidazolylthio(triphenylphosphite)gold and 2-benzoxazolylthio (triphenylphosphite)gold are obtained.

EXAMPLE 12

Substitution of an equivalent amount of a mercapto heterocycle listed below:
 2-mercaptobenzothiazole
 2-mercapto-1-methylimidazole
 2-mercaptothiazole
 2-mercaptooxazole
in the procedure of Example 1 for 2-mercaptothiazoline gives the following S-heterocyclic derivatives of triethylphosphinegold:
 2-benzothiazolylthio(triethylphosphine)gold
 2-(1-methylimidazolyl)thio(triethylphosphine)gold
 2-thiazolylthio(triethylphosphine)gold
 2-oxazolylthio(triethylphospine)gold.

In like manner, the mercapto heterocycles listed above may be allowed to react with the other phosphine or phosphite gold halides disclosed herein.

EXAMPLE 13

| Ingredients | Mg./Tablet |
|---|---|
| 2-Benzoxazolylthio(triethylphosphine)gold | 10 |
| Calcium sulfate dihydrate | 150 |
| Sucrose | 25 |
| Starch | 15 |
| Talc | 5 |
| Stearic acid | 3 |

The sucrose, calcium sulfate and 2-benzoxazolylthio(triethylphosphine)gold are thoroughly mixed and granulated with hot 10% gelatin solution. The wetted mass is passed through a No. 6 mesh screen directly onto drying trays. The granules are dried at 120°F. and passed through a No. 20 mesh screen, mixed with the starch, talc and stearic acid and compressed into tablets.

In a similar manner, the other S-heterocyclic derivatives of phosphine or phosphite gold mercaptides disclosed herein may be formulated into tablets.

What is claimed is:

1. A pharmaceutical composition having anti-arthritic activity, in dosage unit form, comprising a pharmaceutical carrier and an effective but nontoxic amount of a compound of the formula:

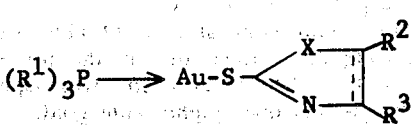

in which:
  $R^1$ is lower alkyl, lower alkoxy, phenyl or phenoxy, with each alkyl or alkoxy having from one to three carbon atoms;
  X is S, NH, $NCH_3$ or O;
  $R^2$ and $R^3$ are hydrogen or together form a 1,2-benzo radical; and
  = indicates an optional double bond.

2. The composition of claim 1 in which $R^1$ is lower alkyl.

3. The composition of claim 2 in which the heterocyclic moiety is 2-thiazolinyl, 2-benzimidazolyl or 2-benzoxazolyl.

4. The composition of claim 3 in which the active medicament is 2-thiazolinylthio(triethylphosphine)gold.

5. The composition of claim 3 in which the active medicament is 2-benzimidazolylthio(triethylphospine)gold.

6. The composition of claim 3 in which the active medicament is 2-benzoxazolylthio(triethylphosphine)gold.

7. The composition of claim 1 in which the active medicament is in an amount of 0.5 mg. to about 25 mg., calculated on gold content, per dosage unit.

8. The method of producing anti-arthritic activity which comprises administering internally to an animal organism in an amount sufficient to produce said activity a compound as defined in claim 1.

9. The method of claim 8 in which $R^1$ is lower alkyl.

10. The method of claim 9 in which the heterocyclic moiety is 2-thiazolinyl, 2-benzimidazolyl or 2-benzoxazolyl.

11. The method of claim 10 in which the active medicament is 2-thiazolinylthio(triethylphosphine)gold.

12. The method of claim 10 in which the active medicament is 2-benzimidazolylthio(triethylphosphine)gold.

13. The method of claim 10 in which the active medicament is 2-benzoxazolylthio(triethylphosphine)gold.

14. The method of claim 8 in which the active medicament is administered in a daily dosage regimen of about 0.5 mg. to about 50 mg., calculated on gold content.

* * * * *

UNITED STATES PATENT AND TRADEMARK OFFICE
CERTIFICATE OF CORRECTION

PATENT NO. : 3,947,565

DATED : March 30, 1976

INVENTOR(S) : Blaine M. Sutton and Joseph Weinstock

It is certified that error appears in the above-identified patent and that said Letters Patent are hereby corrected as shown below:

Column 4, line 8, "(chloro(" should read --chloro(--

Column 4, line 10, "chloro)" should read --chloro(--

Column 4, line 11, "thiazolinylthio)" should read --thiazolinylthio(--

Column 8, line 4, should read --The composition of claim 1 in which $R^1$ is lower--

Signed and Sealed this

Twenty-seventh Day of July 1976

[SEAL]

Attest:

RUTH C. MASON
*Attesting Officer*

C. MARSHALL DANN
*Commissioner of Patents and Trademarks*